(12) United States Patent
Flescher et al.

(10) Patent No.: US 8,349,553 B2
(45) Date of Patent: Jan. 8, 2013

(54) JASMONATE BASED ASSAYS FOR IDENTIFYING COMPOUNDS THAT SELECTIVELY INHIBIT MITOCHONDRIAL BOUND HEXOKINASES

(75) Inventors: Eliezer Flescher, Hod Hasharon (IL); Natalia Goldin, Kfar Hanagid (IL); Max Herzberg, Sitrya (IL)

(73) Assignees: Ramot at Tel Aviv University Ltd., Tel Aviv (IL); Sepal Pharma S.A., Nes-Ziona (IL)

(*) Notice: Subject to any disclaimer, the term of this patent is extended or adjusted under 35 U.S.C. 154(b) by 472 days.

(21) Appl. No.: 12/531,204

(22) PCT Filed: Mar. 16, 2008

(86) PCT No.: PCT/IL2008/000366
§ 371 (c)(1),
(2), (4) Date: Nov. 23, 2009

(87) PCT Pub. No.: WO2008/111088
PCT Pub. Date: Sep. 18, 2008

(65) Prior Publication Data
US 2010/0087384 A1    Apr. 8, 2010

Related U.S. Application Data

(60) Provisional application No. 60/918,032, filed on Mar. 15, 2007.

(51) Int. Cl.
*C12Q 1/00* (2006.01)
(52) U.S. Cl. .............................................. 435/4; 435/14
(58) Field of Classification Search ................ 435/4, 14
See application file for complete search history.

(56) References Cited

U.S. PATENT DOCUMENTS

| 5,854,067 A | 12/1998 | Newgard |
| 5,891,717 A | 4/1999 | Newgard |
| 6,140,007 A | 10/2000 | Watanabe |
| 6,469,061 B1 | 10/2002 | Flescher |

FOREIGN PATENT DOCUMENTS

| WO | 02/080890 A1 | 10/2002 |
| WO | 2005/054172 A1 | 6/2005 |
| WO | 2006/095347 A1 | 9/2006 |
| WO | 2007/066336 A1 | 6/2007 |
| WO | 2007/066337 A1 | 6/2007 |

OTHER PUBLICATIONS

Heyfets et al. "Cooperative cytotoxicity of methyl jasmonate with anti-cancer drugs and 2-deoxy-d-glucose", Cancer Letters, 2007, 250(2):300-310.*
Pastorino et al. "Mitochondrial binding of hexokinase II inhibits bax-induced cytochrome c release and apoptosis", JBC, 2002, 277(9):7610-7618.*
Goldin et al. "Mitochondria-mediated ATP depletion by anti-cancer agents of the jasmonate family", J Bioenerg Biomembr 2007, 39:51-57.*
Robey et al. "Akt, hexokinase, mTOR: targeting cellular energy metabolism for cancer therapy", Drug Discovery Today: disease mechanisms, 2005, 2(2):239-246.*
Kim et al., "Methyl jasmonate induces apoptosis through induction of Bax/Bcl-Xs and activation of caspase-3 via ROS production in A549 cells", Oncology Reports, 12:1233-1238 (2004).
Wilson, J. E., "Hexokinases", Rev. Physiol. Biochem. Pharmacol., 126:65-198 (1995).
Adamczyk, Maciej et al., "Application of surface plasmon resonance toward studies of low-rnolecular-weight antigen-antibody binding interactions", Methods, 20(3):319-328 (2000).
Al Jamal, Jalal A., "Involvement of porin N,N-dicyclohexylcarbodiimide-reactive domain in hexokinase binding to the outer mitochondrial membrane", Protein J, 24(1):1-8 (2005).
Azoulay-Zohar, Heftsi et al., "In self-defence: hexokinase promotes voltage-dependent anion channel closure and prevents mitochondria-mediated apoptotic cell death", Biochem J., 377(pt 2):347-355 (2004).
Boozer, Christina et al., "Looking towards label-free biomolecular interaction analysis in a high-throughput format: a review of new surface plasmon resonance technologies" Curr Opin Biotechnol, 17(4):400-405 (2006).
Crompton, Martin "The mitochondrial permeability transition pore and its role in cell death", Biochem J, 341(pt 2):233-249 (1999).
Fingrut, O. and Flescher, E., "Plant stress hormones suppress the proliferation and induce apoptosis in human cancer cells", Leukemia, 16(4):608-616 (2002).
Fingrut, Orit et al., "Jasmonates induce nonapoptotic death in high-resistance mutant p53-expressing B-lymphoma cells", Br. J. Pharmacol., 146(6):800-808 (2005).
Flescher, Eliezer,"Jasmonates—a new family of anti-cancer agents", Anticancer Drugs, 16(9):911-916 (2005).
Flescher, Eliezer, "Jasmonates in cancer therapy", Cancer Lett, 245(1-2):1-10 (2007).
Galuzzi, L.et al., "Mitochondria as therapeutic targets for cancer chemotherapy", Oncogene, 25(34):4812-4830 (2006).

(Continued)

*Primary Examiner* — Susan Hanley
*Assistant Examiner* — Bin Shen
(74) *Attorney, Agent, or Firm* — Rodney J. Fuller; Booth Udall Fuller, PLC

(57) ABSTRACT

The present invention provides compositions comprising compounds that selectively bind to hexokinases thereby promoting dissociation of these enzymes from mitochondria, and methods of use of such compounds and compositions to induce cell death in diseases and disorders characterized by the high levels of mitochondrial bound hexokinase. The present invention further discloses methods and assays for detecting and identifying molecules having these activities.

11 Claims, 15 Drawing Sheets

OTHER PUBLICATIONS

Gincel, Dan et al., "Calcium binding and translocation by the voltage-dependent anion channel: a possible regulatory mechanism in mitochondrial function", Biochem J, 358(pt 1):147-155 (2001).

Goldin, Natalia et al., "Mitochondria-mediated ATP depletion by anti-cancer agents of the jasmonate family" J Bioenerg Biomembr, 39(1):51-57 (2007).

Goldin, N. et al., "Methyl jasmonate binds to and detaches mitochondria-bound hexokinase", Oncogene, 27(34):4636-4643 (2008).

Heyfets, Alina and Flescher, Eliezer, "Cooperative cytotoxicity of methyl jasmonate with anti-cancer drugs and 2-deoxy-d-glucose", Cancer Lett., 250(2):300-310 (2007).

Ishii, Y. et al., "Induction of differentiation of human myeloid leukemia cells by jasmonates, plant hormones". Leukemia, 18(8):1413-1419 (2004).

Johnson, Diane and Lardy, Henry, "Isolation of liver or kidney mitochondria", Methods in Enzymology, 10: 94-96 (1967).

Kovala, A. Thomas et al., "High-efficiency transient transfection of endothelial cells for functional analysis", FASEB J, 14(15):2486-2494 (2000).

Lofas, Stefan, "Optimizing the hit-to-lead process sing SPR analysis", Assay Drug Dev Technol, 2(4):407-415 (2004).

Mathupala, S. P. et al., "Hexokinase II: Cancer's double-edged sword acting as both facilitator and gatekeeper of malignancy when bound to mitochondria", Oncogene, 25(34):4777-4786 (2006).

Pastorino John G. et al., "Mitochondrial binding of hexokinase II inhibits Bax-induced cytochrome c release and apoptosis", J Biol Chem, 277(9):7610-7618 (2002).

Reichmann, D. et al., "The modular architecture of protein—protein binding interfaces", Proc Natl Acad Sci U S A, 102(1):57-62 (2005).

Reischer, D. et al., "Effects of natural and novel synthetic jasmonates in experimental metastatic melanoma", Br J Pharmacol, 150(6):738-749 (2007).

Robey, R. B. and Hay, N., "Mitochondrial hexokinases, novel mediators of the antiapoptotic effects of growth factors and Akt", Oncogene, 2(34):4683-4696 (2006).

Rotem, R. et al., "The anticancer agent methyl jasmonate induces activation of stress-related c-Jun N-terminal kinase and p38 protein kinase in human lymphoid cells", Leukemia, 17(11):2230-2234 (2003).

Rotem, Ronit et al., "Jasmonates: novel anticancer agents acting directly and selectively on human cancer cell mitochondria", Cancer Res., 65(5):1984-1993 (2005).

Shoshan-Barmatz, V. and Israelson, A., "The voltage-dependent anion channel in endoplasmic/sarcoplasmic reticulum: characterization, modulation and possible function", J Membr Biol., 204(2):57-66 (2005).

Varbiro, Gabor et al., "Direct effect of Taxol on free redical formation and mitochondrial permeability transition", Free Radic Biol Med. 31(4):548-558 (2001).

Wilson, John E., "Isozymes of mammalian hexokinase: structure, subcellular localization and metabolic function", J Exp Biol, 206(pt 12):2049-2057 (2003).

Yeruva, L. et al., "Jasmonates induce apoptosis and cell cycle arrest in non-small cell lung cancer lines", Exp Lung Res, 32(10):499-516 (2006).

Zaid, H. et al., "The voltage-dependent anion channel-1 modulates apoptotic cell death", Cell Death Differ., 12(7):751-760 (2005).

* cited by examiner

Eth    MJ 1mM    MJ 2mM    MJ 3mM    JA 3mM    G6P 0.5mM

HKI

HKII

US 8,349,553 B2

JASMONATE BASED ASSAYS FOR IDENTIFYING COMPOUNDS THAT SELECTIVELY INHIBIT MITOCHONDRIAL BOUND HEXOKINASES

RELATED APPLICATION DATA

This application is the U.S. national stage of PCT/IL2008/000366 filed Mar. 16, 2008, which claims the benefit of U.S. Provisional Application No. 60/918,032, filed Mar. 15, 2007, the contents of each of which are herein incorporated by reference for all purposes.

FIELD OF THE INVENTION

The present invention relates to assays for determining anti-tumor effects of candidate drug molecules. The invention specifically relates to methods of identifying chemical compounds that selectively bind to hexokinases thereby promoting dissociation of these enzymes from mitochondria, to compositions comprising such compounds and to methods of using such compositions to induce cell death in diseases and disorders characterized by the high levels of mitochondrial bound hexokinase.

BACKGROUND OF THE INVENTION

Hexokinases

Hexokinase is the initial and key enzyme in the glycolytic pathway which involves a sequence of enzymatic reactions that oxidize glucose to produce compounds which are subsequently either fully metabolized by the mitochondria to produce carbon dioxide and ATP or used for the synthesis of fat for storage. The hexokinase isozymes I, II, and III can physically associate to the outer surface of the external membrane of mitochondria through specific binding to a voltage dependent anion channel. This association is known to prevent mitochondria-mediated apoptotic cell death. In cancer cells, mitochondria-bound hexokinase as well as hexokinase (mostly of type I and II) bound to voltage dependent anion channel are over-expressed. The elevated levels of mitochondria-bound hexokinase in cancer cells is suggested to play a pivotal role in cancer cell growth rate and survival, by improving energy supply and protecting against mitochondria-mediated cell death. Recently, hexokinase type II has been suggested as a prospective target of anti-cancer therapy (Mathupala, 2006).

The mitochondrion is well known for its ability to produce ATP and to regulate cellular metabolism. In addition, the mitochondria play a key role in controlling cell death. Upon exposure to adverse conditions, permeability transition of the mitochondria can be initiated. The permeability transition pore complex (PTPC) is governed by three major components, namely adenine nucleotide translocator, cyclophilin D, and voltage-dependent anion channel. Prolonged opening of the PTPC leads to dissipation of inner membrane mitochondrial potential, osmotic swelling of the mitochondrial matrix, subsequent release of cytochrome c, and finally cell death by either necrosis or apoptosis (Galuzzi, 2006).

U.S. Pat. Nos. 5,854,067 and 5,891,717 disclose compositions and methods for inhibiting hexokinase enzymes in mammalian cells. The references provide proteins that stimulate the production of trehalose-6-phosphate and their respective genes; hexokinase-specific ribozymes and genes encoding such constructs; and agents that competitively reduce hexokinase activity, e.g., by displacing hexokinase from mitochondria, and their respective genes. The latter group of agents includes inactive hexokinases and fragments thereof that retain mitochondrial binding functions and hexokinase-glucokinase chimeras that further substitute glucokinase activity for hexokinase activity. Indicators of altered mitochondrial function in predictive methods for determining the risk of type 2 diabetes mellitus have been disclosed in U.S. Pat. No. 6,140,067.

Jasmonates

Plant stress hormones of the jasmonate family were previously found to be endowed with anti-cancer capabilities (Ishii, 2004; Kim, 2004). Jasmonates are small hydrophobic molecules capable of prolonging the survival of tumor-bearing animals. The jasmonates were shown to be cytotoxic towards cancer cell lines, both in vitro and ex-vivo in cells drawn from cancer patients. Importantly, jasmonates are selectively toxic towards cancer cells versus normal cells. In the leukemic cell line Molt-4, the cytotoxicity of methyl jasmonate (MJ) was shown to be transcription—as well as translation-independent. In addition, jasmonates overcome drug resistant phenotypes and exhibit anti-metastatic effects (Fingrut, 2002; Fingrut, 2005; Heyfets, 2007; Flescher, 2005; Reischer, 2007).

Use of jasmonates for the treatment of mammalian cancer has been disclosed in U.S. Pat. No. 6,469,061. Specifically, it was shown that jasmonates were directly cytotoxic for various types of human cancer cells derived from breast, prostate, skin and blood cancers. While jasmonates elicited death in human leukemic Molt-4 cells, they did not damage normal lymphocytes. In particular, methyl jasmonate was shown to be effective in preventing the development of lymphomas in mice (Fingrut, 2002). International Patent Publication WO 02/080890 further teaches that jasmonates do not damage healthy erythrocytes.

International Patent Publication WO 05/054172 discloses novel halogenated jasmonate derivatives, pharmaceutical compositions comprising same, and their use for reducing cancer cell growth and for treating cancer.

International Patent Publications WO 07/066,336 and WO 07/066,337 disclose chemical derivatives of jasmonate compounds, methods for their preparation, pharmaceutical compositions including same, and methods of using these compounds and compositions, especially as chemotherapeutic agents for treatment of cancers in mammals, and in particular humans.

Recently, jasmonates were shown to directly affect mitochondria of cancer cells from several different cancer cell lines, as well as from lymphocytes of chronic lymphocytic leukemia patients. The proposed mechanism by which jasmonate act is PTPC-mediated through voltage dependent anion channel whose opening was found to induce jasmonate mitochondrial perturbation (Rotem, 2005; Robey, 2006). In contrast, jasmonates did not show toxicity nor did they induce mitochondrial perturbation in normal lymphocytes and in non-transformed 3T3 cells (Fingrut, 2002; Rotem, 2005).

Voltage dependent anion channel compositions including polynucleotides encoding same and variants thereof, as well as peptide fragment, peptide derivatives and analogs were disclosed in International Patent Publication WO 06/095347. WO 06/095347 discloses methods of using voltage dependent anion channel compositions for regulating apoptosis.

The composition and function of mitochondria in cancer cells in comparison to normal cells differ in numerous aspects, including PTPC components, membrane potential, and ATP generation (Mathupala, 2006). These differences may account for the selective activity of jasmonates on cancer cells. Jasmonates were also shown to cause a significant drop in ATP cellular content in cancer cells. This drop was not detected in normal cells (Fingrut, 2005; Heyfets, 2007; Goldin, 2007). Moreover, a positive correlation was found to exist between the susceptibility of a given cell type to the cytotoxic effect of methyl jasmonate and the degree of ATP depletion induced in that cell (Goldin, 2007).

There remains an unmet need for highly reliable assays for identifying drug candidates having anti-tumor activity. Such assays may be used to identify effective anticancer drugs, with few of the adverse side effects of known anti-cancer modalities. In addition, there is an unmet need for new therapeutic agents to produce an improved outcome in preventing the progression or inducing the regression of established tumors, or for preventing metastases.

SUMMARY OF THE INVENTION

The present invention provides an assay that is based on the interaction of natural or synthetic jasmonates with certain specific target molecules. In particular, the invention discloses an assay designated for determining the anti-tumor effect of a candidate drug molecule by comparing its activity to the activity of a jasmonate known to dissociate hexokinase from mitochondria. Anticancer drug candidate molecules identified by the assay and methods of using same to inhibit cancer cell proliferation are disclosed as well.

The present invention is based in part on the unexpected discovery that the hexokinase as well as its association with voltage-dependent anion channel comprise the molecular targets of jasmonates. It is now disclosed for the first time that methyl jasmonate (MJ) dissociates hexokinase from mitochondria, and interferes with hexokinase binding to voltage-dependent anion channel by directly binding to it. Furthermore, methyl jasmonate perturbs only hexokinase that is bound to mitochondria, thus leaving the metabolism of normal cells largely unaffected.

According to a first aspect, the present invention provides an assay for identifying a chemical compound having an anti-tumor effect comprising comparing the activities of the compound and a jasmonate derivative known to have anti-tumor activity in at least one of the following: dissociating hexokinase from mitochondria, interfering with hexokinase binding to a voltage dependent anion channel, and binding to hexokinase directly; wherein an equal or greater activity of the compound as compared with the jasmonate derivative is indicative of the anti-tumor effect of the compound.

In a second aspect, the present invention provides an assay for identifying a chemical compound having an anti-tumor effect comprising: introducing the compound into a cell free system comprising mitochondria, measuring the ability of the compound to induce dissociation of a hexokinase from mitochondria, and comparing the dissociation of hexokinase in the presence of the compound to the dissociation achieved by a comparable concentration of a jasmonate derivative known to have anti-tumor activity; wherein an equal or greater dissociation in the presence of the compound is indicative of an anti-tumor effect of the compound.

In yet another aspect, the present invention provides an assay for identifying a chemical compound having an anti-tumor effect comprising: measuring the direct binding of the compound to at least one hexokinase subtype and comparing this binding to the binding achieved by a comparable concentration of a jasmonate derivative known to have anti-tumor activity, wherein an equal or greater binding in the presence of the compound is indicative of the anti-tumor effect of the compound. In a currently preferred embodiment, the compound selectively induces tumor cell death.

According to certain embodiments, the jasmonate derivative known to have anti-tumor activity is methyl jasmonate or a synthetic jasmonate derivative as known in the art.

In other embodiments, the present invention provides an assay for identifying a candidate drug molecule having an anti-tumor effect, wherein the candidate drug molecule is a jasmonate derivative other than methyl jasmonate. In another embodiment, the present invention provides an assay for identifying a candidate drug molecule having an anti-tumor effect, wherein the candidate drug molecule is a non-peptide small organic molecule.

In some embodiments, the present invention provides a unique assay for identifying small molecules (e.g., non-peptide molecules) having high specificity towards malignant cells. According to certain embodiment, the small molecules have molecular weight of less than about 2,000 grams per mole (i.e., a MW of less than about 2000), more preferably less than about 1,500 grams per mole (i.e., a MW of less than about 1,500), and most preferably less than about 1,000 grams per mole (i.e., a MW of less than about 1,000). Compound identified by the assay of the present invention can be naturally occurring, synthetic, or can include both natural and synthetic components.

Accordingly, the present invention provides an assay for determining the anti-tumor effect of a candidate drug molecule. In yet other embodiments, the present invention provides an anticancer drug candidate molecule identified by an assay comprising comparing the activity of the candidate drug molecule to the activity of methyl jasmonate in at least one of the following: dissociating hexokinase from mitochondria, interfering with hexokinase binding to a voltage dependent anion channel, and binding to hexokinase directly.

The anticancer drug candidate molecules identified by the assay of the present invention can be tested for their activity and efficacy according to any known method in the art. According to certain embodiments, the drug candidates can be tested in a form suitable for oral administration (e.g., a solution, a suspension, a syrup, an emulsion, a dispersion, a suspension, a tablet, a pill, a capsule, a pellet, granules and a powder), for parenteral administration (e.g., intravenous, intramuscular, intra-arterial, transdermal, subcutaneous or intraperitoneal), for topical administration (e.g., an ointment, a gel, a cream), for administration by inhalation or for administration via suppository.

In some embodiments, the present invention provides a drug candidate wherein the drug candidate is administered in a pharmaceutical composition. In a currently preferred embodiment, the drug candidate of the invention is administered in a composition further comprising a pharmaceutically acceptable carrier or diluent.

In certain embodiments, the present invention additionally provides a method for inhibiting cancer cell proliferation, comprising contacting the cancer cells with a therapeutically effective amount of a compound identified by an assay as described herein.

Furthermore, the present invention provides a method for the treatment of cancer in a subject, by administering to the subject a therapeutically effective amount of the compound of the invention, as described herein. In some embodiments, the compound is administered in a pharmaceutical composition. Preferably, a compound of the invention is administered in a composition further comprising a pharmaceutically acceptable carrier or diluent.

According to other embodiments, the compounds identified by the assays of the present invention are active against a wide range of cancers including, but not limited to, carcinoma, sarcoma, adenoma, hepatocellular carcinoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, lymphagiosarcoma, synovioma, Ewing's tumor, leiomyosarcoma, rhabdotheliosarcoma, colon carcinoma, pancreatic cancer, breast cancer, ovarian cancer, prostate cancer, squamous cell carcinoma, basal cell carcinoma, adenocarcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small cell and non-small cell lung carcinoma, bladder carcinoma, epithelial carcinoma, glioma, astrocytoma, medulloblastoma, craniopharyngioma, ependynoma, pinealoma, retinoblastoma multiple myeloma, rectal carcinoma, cancer of the thyroid, head and neck cancer, brain cancer, cancer of the peripherial nervous system, cancer of the central nervous system, neuroblastoma, cancer of the endometrium, lymphoproliferative diseases, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma, as well as metastasis of all the above.

According to another aspect, the present invention provides a pharmaceutical composition comprising a compound identified by an assay according to the present invention for inhibiting cancer cell proliferation. In certain embodiments, the pharmaceutical composition further comprises a pharmaceutically acceptable carrier or diluent. In other embodiments, the present invention provides a pharmaceutical composition comprising a compound identified by an assay according to the present invention for treating cancer.

According to yet another aspect, the present invention relates to the use of a compound identified by an assay according to the present invention for inhibiting cancer cell proliferation in a subject. In other embodiments, within the scope of the present invention is the use of a compound identified by an assay according to the present invention for treating cancer. In one embodiment, the subject is a mammal, preferably a human.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1. Methyl jasmonate (MJ) detaches hexokinase (HK) from mitochondrial fractions of CT-26 tumor.

FIG. 4. Methyl jasmonate (MJ) depletes cellular ATP during 60 minutes of exposure.

FIG. 6. Methyl jasmonate (MJ) binds to hexokinase in a specific and dose-dependent manner.

FIG. 7. Methyl jasmonate (MJ) detaches hexokinase from mitochondrial fractions of mouse brain.

FIG. 8. Methyl jasmonate (MJ) causes swelling in mouse brain but not in mouse liver mitochondrial fractions.

FIG. 9. Over-expression of hexokinase protects against methyl jasmonate-induced ATP depletion and cytotoxicity. CT26 cells were transfected with a hexokinase II-expressing vector (grey) or control plasmid (white).

DESCRIPTION OF PREFERRED EMBODIMENTS OF THE INVENTION

Figure 1A:
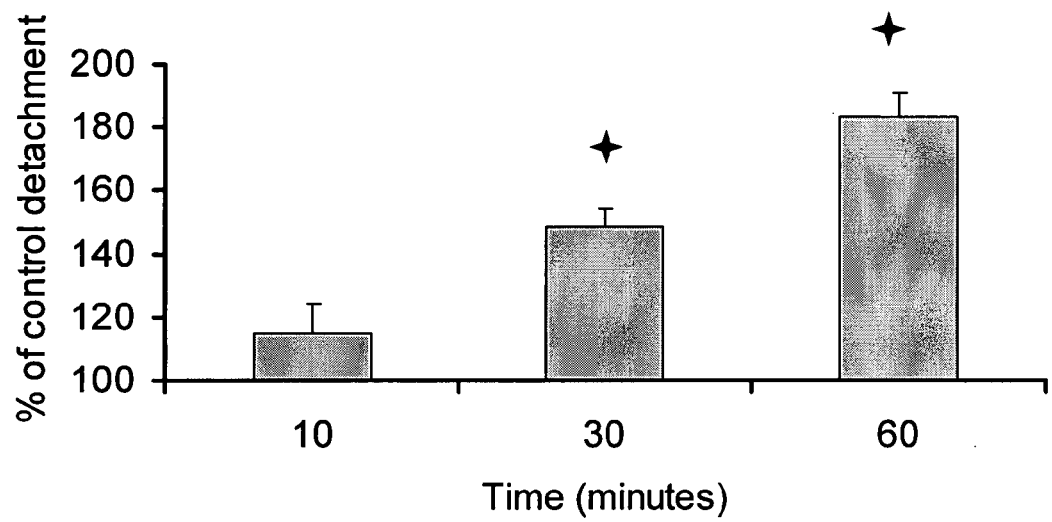
FIG. 1A. Methyl jasmonate (MJ; 3 mM) detaches hexokinase in a time-dependent manner.

The present invention provides novel assays based on specific subcellular targets, and are based on the discovery that certain jasmonates interfere with cellular metabolism thereby leading specifically to death of malignant cells without significantly affecting normal cell populations adversely. The present invention additionally provides assays to identify and select novel small molecules exerting specific anti-cancer activities via these newly identified subcellular targets.

In one embodiment, the invention is directed towards jasmonates as important new class of selective anti-cancer drugs. Without being bound by any theory or mechanism of action, it is contemplated that jasmonates appear to act, at least in part, via perturbation of the mitochondrial hexokinases as well as other ATP generating pathways including cytosolic glycolytic pathways. The positive correlation between the susceptibility of a given cell type to the cytotoxic effect of methyl jasmonate and the consequent reduction in ATP induced in that cell was found to be independent of pyruvate and oligomycin (the substrate and the inhibitor of oxidative phosphorylation, respectively). This suggests that the effect of methyl jasmonate on the mitochondrial ATP generation is massive and irreversible. On the contrary, the glycolysis substrate glucose showed a protective effect against methyl jasmonate-induced ATP drop, whereas the glycolysis inhibitor 2-deoxyglucose showed synergistic effects when combined with methyl jasmonate (Fingrut, 2005; Heyfets, 2007).

Identification of pathways involved in jasmonate induced cell death will enable selection of the clinical settings in which jasmonates would be effective as anti-cancer agents, as well as enabling clinicians to estimate their potential side effects. Moreover, identification of target molecules with which these anti-cancer agents interact, allows rational design of more potent jasmonate derivatives as well as characterization or design of other small organic molecules that interact with the same or similar target molecules.

According to one aspect, the present invention provides an assay for determining the anti-tumor effect of a candidate drug molecule comprising comparing the activity of the candidate drug molecule to the activity of methyl jasmonate in at least one of the following: dissociating hexokinase from mitochondria, interfering with hexokinase binding to a voltage dependent anion channel, and binding to hexokinase directly. Additionally, the invention provides an assay for the potential anti-tumor effect of a non-peptide small organic molecule.

According to another aspect, the present invention provides an anticancer drug candidate molecule identified by any one of the assays disclosed in the present invention. The anticancer drug candidate molecules can be subsequently tested for their activity and efficacy according to any known method in the art.

According to other embodiments, the drug candidates can be tested in a form suitable for oral administration (e.g., a solution, a suspension, a syrup, an emulsion, a dispersion, a suspension, a tablet, a pill, a capsule, a pellet, granules and a powder), for parenteral administration (e.g., intravenous, intramuscular, intra-arterial, transdermal, subcutaneous or intraperitoneal), for topical administration (e.g., an ointment, a gel, a cream), for administration by inhalation or for administration via suppository.

Additionally, the drug candidates can be tested as pharmaceutical compositions further comprising any acceptable diluent and/or carrier. The carriers may be any of those conventionally used and can be chosen according to the preferred route of administration. Exemplary suitable carriers include, but are not limited to, lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. The drug candidates can additionally include lubricating agents such as talc, magnesium stearate, and mineral oil; wetting agents, surfactants, emulsifying and suspending agents; preserving agents such as methyl- and propylhydroxybenzoates; sweetening agents; flavoring agents, colorants, buffering agents (e.g., acetates, citrates or phosphates), disintegrating agents, moistening agents, antibacterial agents, antioxidants (e.g., ascorbic acid or sodium bisulfite), chelating agents (e.g., ethylenediaminetetraacetic acid), and agents for the adjustment of tonicity such as sodium chloride. Other pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions.

The present invention additionally provides a method for inhibiting cancer cell proliferation, comprising contacting the cancer cells with a therapeutically effective amount of a compound identified by an assay as described herein. The term "inhibiting cancer cell proliferation" in the context of the present invention refers to a decrease in at least one of the following: number of cells (due to cell death which may be necrotic, apoptotic or any other type of cell death or combinations thereof) as compared to control; decrease in growth rates of cells, i.e. the total number of cells may increase but at a lower level or at a lower rate than the increase in control; decrease in the invasiveness of cells (as determined for example by soft agar assay) as compared to control even if their total number has not changed; progression from a less differentiated cell type to a more differentiated cell type; a deceleration in the neoplastic transformation; or alternatively the slowing of the progression of the cancer cells from one stage to the next.

Furthermore, the present invention provides a method for the treatment of cancer in a subject, by administering to the subject a therapeutically effective amount of the compound identified by the assay systems of the invention, as described herein. The term "treatment of cancer" in the context of the present invention includes at least one of the following: a decrease in the rate of growth of the cancer (i.e. the cancer still grows but at a slower rate); cessation of growth of the cancerous growth, i.e., stasis of the tumor growth, and, in preferred cases, the tumor diminishes or is reduced in size. The term also includes reduction in the number of metastasis, reduction in the number of new metastasis formed, slowing of the progression of cancer from one stage to the other and a decrease in the angiogenesis induced by the cancer. In most preferred cases, the tumor is totally eliminated. Additionally included in this term is lengthening of the survival period of the subject undergoing treatment, lengthening the time of diseases progression, tumor regression, and the like. This term also encompasses prevention for prophylactic situations or for those individuals who are susceptible to contracting a tumor.

A "therapeutically effective amount" as used herein refers to the amount of compound which is sufficient to provide a beneficial effect to the subject to which the compound is administered. The term "cancer" in the context of the present invention includes all types of neoplasm whether in the form of solid or non-solid tumors, and includes both malignant and premalignant conditions as well as their metastasis. Cancers may be classified in two ways: by the type of tissue in which the cancer originates (histological type) and by primary site, or the location in the body where the cancer first developed. The international standard for the classification and nomenclature of histologies is the International Classification of Diseases for Oncology, Third Edition.

The compounds identified by the assays of the present invention are active against a wide range of cancers including, but not limited to, carcinoma, sarcoma, adenoma, hepatocellular carcinoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, lymphagiosarcoma, synovioma, Ewing's tumor, leiomyosarcoma, rhabdotheliosarcoma, colon carcinoma, pancreatic cancer, breast cancer, ovarian cancer, prostate cancer, squamous cell carcinoma, basal cell carcinoma, adenocarcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small cell and non-small cell lung carcinoma, bladder carcinoma, epithelial carcinoma, glioma, astrocytoma, medulloblastoma, craniopharyngioma, ependynoma, pinealoma, retinoblastoma, multiple myeloma, rectal carcinoma, cancer of the thyroid, head and neck cancer, brain cancer, cancer of the peripherial nervous system, cancer of the central nervous system, neuroblastoma, cancer of the endometrium, lymphoproliferative diseases, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma, as well as metastasis of all the above.

Within the scope of the present invention are methods for inhibiting cancer cell proliferation, and methods for the treatment of cancer in a mammal, by administering to the mammal a therapeutically effective amount of the compounds identified by the assays disclosed herein. In one embodiment, the mammal is human. However, the present invention also contemplates using the compounds of the present invention for non-human mammals, e.g., in veterinary medicine.

The present invention provides unique assays for identification of non-peptide small molecules having high specificity towards malignant cells. "Small molecule" as used herein, is meant to refer to a composition or compound, which has a molecular weight of less than about 2,000 grams per mole (i.e., a MW of less than about 2,000) more preferably less than about 1,500 grams per mole (i.e., a MW of less than about 1,500), and most preferably less than about 1,000 grams per mole (i.e., a MW of less than about 1,000). Compound identified by the assay of the present invention can be naturally occurring, synthetic, or can include both natural and synthetic components including, but not limited to, carbohydrates, lipids and other non-peptide organic molecules. In one embodiment, the novel small molecules identified by the methods of the present invention are more potent than the reference jasmonate derivative compound used in the assay to discover them. They therefore will display cytotoxic effects with a high degree of specificity towards malignant cells.

The principles of the present invention are demonstrated by means of the following non-limitative examples.

EXAMPLES

Materials

All reagents were purchased from Sigma Chemicals (St Louis, Mo., USA) unless otherwise stated. Methyl jasmonate (MJ) and jasmonic acid (JA) were dissolved in ethanol to give a stock solution of 500 mM. Further dilutions were performed in culture medium or assay buffer. The final concentration of ethanol in tests did not exceed 0.6%. For surface plasmon resonance experiments, methyl jasmonate was diluted in DMSO to give a stock solution of 500 mM. Taxol was purchased from MeadJohnson, USA. Hydroxyapatite (Bio-Gel HTP) was purchased from Bio-Rad Laboratories (Hercules, Calif., USA). Celite was purchased from BDH (Poole, Dorset, UK). PEGFP plasmid was purchased from Clontech, CA, USA. PcDNA3.1 plasmid was purchased from Invitrogen, CA, USA. PcDNA3.1 HKII was kindly provided by Dr. J. E. Wilson, University of Michigan.

Animals

Wistar female rats and ICR male mice were used for brain and liver extraction. BALB/c and C57BL male mice (7-8 weeks old) were obtained from the breeding colony of Tel-Aviv University, Israel, and were used to grow BCL1 leukemia, B16 and CT26 tumors. Animal care and experimentation were carried out in accordance with Tel-Aviv University guidelines and approved by the Institutional Animal Use and Care Committee. Mice were kept in cages under standard food and housing conditions.

Cancer Cell Lines and Tumors

CT26 murine colon carcinoma cell line, B16 murine melanoma cell line, BCL1 murine B cell leukemia cell line, and Molt-4 human T lymphoblastic leukemia cell line, were purchased from ATCC (Rockville, Md., USA). The cells were maintained in a humidified atmosphere, at 37° C. with 5% $CO_2$. CT26 and B16 cells were maintained in Dulbecco's modified Eagle's medium (Biological Industries, Beit-Haemek, Israel), supplemented with 10% FCS, 2 mM L-glutamine, 100 U $ml^{-1}$ penicillin, 100 µg $ml^{-1}$ streptomycin, 1 mM sodium pyruvate and 1:100 dilution of nonessential amino acids (all purchased from Biological Industries, Israel). Molt-4 and BCL1 cells were maintained in RPMI-1640 medium (Biological Industries, Israel), supplemented with 10% FCS, 2 mM L-glutamine, 100 U $ml^{-1}$ penicillin and 100 µg $ml^{-1}$ streptomycin.

BCL1 cells were grown in BALB/c mice as described in Heyfets and Flescher (2007). Extraction of BCL1 cells: $10^6$ BCL1 cells, freshly extracted from BCL1 leukemia bearing BALB/c mice, were inoculated intra-peritoneally (i.p.) into mice in 100 µl PBS to produce tumor growth. Four weeks later the mice were killed under anesthesia and their spleens were extracted. The cells were extracted by spleen dispersion. RBC were disrupted using the RBC lysis buffer (Sigma).

Solid tumors preparation: $10^6$ CT26 cells or B16 cells were injected subcutaneously in 100 μl PBS in both flanks. The tumors were excised upon reaching diameter of 10-12 mm, exhibiting no necrotic signs.

Cytotoxicity Determination

Cell death was determined by trypan blue exclusion. Upon completion of a given experiment, cells were incubated with 0.1% trypan blue for 2-5 minutes and the percentage of dead cells (those cells that did not exclude the dye) was determined microscopically (Fingrut, 2002). Alternatively, cytotoxicity was determined using hemacolor staining. Upon completion of a given experiment, cells were stained and the percentage of dead (detached) cells was determined spectrophotometrically.

Determination of ATP Levels

The CellTiter-Glo™ Luminescent Cell Viability Assay (Promega, Madison, Wis., U.S.A.) was employed (Fingrut, 2005). Upon completion of a given experiment, plates were equilibrated to room temperature. CellTiter-Glo™ reagent containing luciferin and luciferase was added to each well and the plates were mixed on an orbital shaker for 2 minutes to induce cell lysis. In the presence of ATP, $Mg^{2+}$ and molecular oxygen, mono-oxidation of luciferin is catalyzed by luciferase, generating a luminescence signal. Cells were then incubated for 10 minutes at room temperature to stabilize the luminescence signal. Luminescence was recorded using Kodak digital science—Image station 440 CD. Luminescence is directly proportional to ATP concentration. ATP depletion (% of control) was calculated in the following way: {(luminescence of control cells−luminescence of drug-treated cells)/luminescence of control cells}×100.

Extraction of Mitochondrial Fraction

Mitochondrial fraction was prepared by mechanical lysis and differential centrifugation. All stages were performed on ice. Cells or extracted tissues were washed with PBS and disrupted by homogenization in extraction buffer (Sucrose 250 mM, HEPES-NaOH 10 mM, pH 7.2) freshly supplemented with 0.1 mM EDTA and Protease Inhibitors cocktail (Sigma). For each gram of cells or tissue, 4 volumes of extraction buffer were applied. The homogenate volume was doubled with the extraction buffer, and tissue and cell debris as well as nuclei were pelleted by centrifugation of 1,000 g for 10 minutes. The supernatant was further spun at 13,000 g for 10 minutes twice. Endoplasmic reticulum layer was removed. The pellet, designated as the mitochondrial fraction, was suspended in the appropriate buffer, depending on the assay for which the mitochondrial fraction was prepared. Mitochondrial fractions were used immediately or stored at −196° C.

Hexokinase Detachment Assay

To determine the amount of hexokinase detached from the mitochondrial fraction by different agents, mitochondria were incubated with the agent of interest and pelleted by centrifugation. Activity of hexokinase in the supernatant (i.e., activity of the detached hexokinase) was determined spectrophotometrically at 340 nm. The reaction couples the ADP formation by hexokinase, consuming the ADP for pyruvate formation by pyruvate kinase, and reducing the pyruvate with NADH by lactate dehydrogenase. Briefly, mitochondria were suspended in incubation buffer (HEPES pH 7.4 20 mM, Sucrose 0.25M, Glucose 10 mM, KCl 5 mM, $MgCl_2$ 10 mM; 0.2 mg/test, 100 μL/test) and incubated as described below. Mitochondria-bound hexokinase was precipitated by centrifugation at 20,000 g for 10 minutes at 4° C. The activity of hexokinase in the supernatant fraction was assayed in reaction buffer (250 μL; HEPES pH 7.2 20 mM, $MgCl_2$ 5 mM, KCl 5 mM, glucose 10 mM) freshly supplemented with pyruvate kinase (1 U/ml), lactate dehydrogenase (1 U/ml), ATP (1 mM), phospho(enol)pyruvate (1 mM), NADH (0.18 mg/ml). Under these conditions, neither methyl jasmonate nor jasmonic acid added directly to the assay mixture, influence hexokinase activity.

Western Blot

For analysis of hexokinase levels, the experiments were performed similarly to hexokinase detachment assay described above, and unbound hexokinase in the supernatant fraction was extracted as described in Fingrut (2005). Samples were separated by sodium dodecylsulfate-polyacrylamide gel (7%) electrophoresis followed by immunoblotting. The blots were probed with specific anti-HKI or anti-HKII antibodies (1:300, Santa-Cruz Biotechnology, CA, USA). Hexokinase-antibody complexes were stained with HRP-conjugated antibody (1:10,000, Santa-Cruz Biotechnology, CA, USA). Enhanced chemiluminescence (ECL) reagent (Biological Industries, Beit Haemek, Israel) was added, and the blots were exposed to ECL film (Eastman Kodak, Rochester, N.Y., USA).

Determination of Cytochrome c Release from Mitochondrial Fraction

Freshly isolated mitochondrial fraction, at a final concentration of 2 mg/ml in a volume of 100 μL, was incubated at 37° C. with the examined agent, e.g. methyl jasmonate, in a KCl-based respiratory buffer (150 mM KCl, 25 mM $NaHCO_3$, 1 mM $MgCl_2$, 3 mM $KH_2PO_4$, 20 mM Hepes, pH 7.4; Pastorino, 2002). Potassium succinate (5 mM) was added as respiratory substrate (Azoulay-Zohar, 2004). For the determination of cytochrome c release, mitochondrial fraction was pelleted at 20,000×g for 10 minutes at 4° C. Pellets were incubated for 40 minutes with lysis buffer (Tris HCl, pH 8, 20 mM, NaCl 137 mM, EDTA 2 mM, pH 8, 1% Triton-X-100, Protease Inhibitors cocktail: Sigma) on ice (Fingrut, 2005). Pellet lysates and supernatants were separated on 12% SDS-PAGE gels and electroblotted onto nitrocellulose membranes. Cytochrome c was detected by specific antibody (1:1000, BD PharMingen, San Diego, Calif.). Antigen-antibody complexes were stained with horseradish peroxidase-conjugated antibody (1:10,000, Santa Cruz Biotechnology, CA) and enhanced chemiluminescence (ECL) reagent (EZ-ECL, Biological Industries, Beit Haemek, Israel), and exposed to ECL film (Eastman Kodak, Rochester, N.Y., U.S.A.).

Mitochondrial Swelling Assay

Freshly isolated mitochondrial fraction was washed with extraction buffer to remove EDTA and resuspended in swelling buffer (Mannitol 220 mM, Sucrose 70 mM, Tris, pH 7.2, 150 mM, $KH_2PO_4$, pH 7.2, 0.2 mM; 0.2 mg in 100 μL) freshly supplemented with potassium succinate, pH 7.2, 5 mM. Every component was sodium-free. Optical density was monitored at the wave length of 540 nm for 2-5 minutes before the addition of the examined reagents, e.g. methyl jasmonate, and for additional 20 minutes afterwards.

Hexokinase Purification

Rat brain HK-I was purified as following, crude brain mitochondria containing tightly bound HK-I were incubated with 1.2 mM glucose-6-phosphate and 0.5 mM K-EDTA to release the enzyme into the soluble fraction. Further purification of HK-I was achieved by affinity chromatography on Cibacron Blue-agarose (Pharmacia). The purified enzyme was concentrated and washed in 0.5 mM K-EDTA, 10 mM glucose, 1 mM dithiothreitol and 10 mM K-Hepes, pH 7.8, using an Amicon device and a 50,000 Da molecular mass cut-off membrane (Spectrum; type C). The concentrated enzyme (up to 1 mg/ml; 30-60 units/mg) was frozen in liquid nitrogen and stored at −80° C. until use (Azoulay-Zohar, 2004).

Surface Plasmon Resonance Analysis of Jasmonate-HK Interactions

Surface plasmon resonance (SPR) is an optical biosensor technique that measures molecular binding events at a metal surface by detecting changes in the local refractive index. SPR is the surface-sensitive technique ideal for studying interactions between immobilized biomolecules (ligands) and a solution-phase analyte. The biosensor response is directly proportional to the mass of the bound analyte. The advantage of SPR for investigation of small molecular weight analytes over conventional techniques such as fluorescence or enzyme-linked immunosorbent assay is detection of an analyte being label-free and direct, without the need for labeling of analyte or multistep detection protocols (sandwich assay). Also, SPR is capable of detecting analytes over a wide range of binding affinities.

SPR using ProteOn-EP5 (Bio-Rad, Hercules, Calif., USA) system has been applied to study the direct interaction of methyl jasmonate with hexokinase. This system allowed measuring ligand-analyte interactions in a 6×6 format in real time. Purified rat brain HKI and rabbit immunoglobulin G (Rb IgG; ligands) were diluted in 10 mM Na acetate pH 4 and 4.5, respectively, and coupled to a GLM sensor surface activated with 37.5 mg/ml N-Ethyl-N'-(3' dimethylaminopropyl) carbodiimide hydrochloride and 7.5 mg/ml N-hydroxysuccinimide. HKI and IgG were added to saturate the chip at 100 μg/ml. Remaining reactive groups on the chip were then inactivated with 1 M ethanolamine pH 8.5. The basic signal of hexokinase at saturation was between 8200 and 9000 relative units (RU), and that of Rb IgG-10500 RU. Methyl jasmonate and jasmonic acid (analytes) were diluted in running buffer (PBS X 1 with 0.005% Tween and 5% DMSO) and injected onto the sensor chip at varying concentrations. All experiments were performed at flow rate of 50 μl/min, at 25° C. Results are representative sensograms of at least 3 experiments. The maximal relative units were about 60 RU. The signals were normalized using appropriate negative controls.

Voltage-Dependent Anion Channel Purification

Voltage-dependent anion channel was purified as described in Azoulay-Zohar (2004). Briefly, rat liver mitochondria (200 mg of protein) were incubated for 30 minutes at 0° C. (at 5 mg/ml) in a solution containing 10 mM Tris, pH 7.0, 0.15 mM PMSF, 0.5 μg/ml leupeptin and 0.05% lauryl (dimethyl)amine oxide (LDAO). After centrifugation at 44,000 g for 20 minutes, the pellet was resuspended at 5 mg/ml in the above solution containing 2% LDAO. After centrifugation at 44,000 g for 30 minutes, the LDAO-extracted voltage-dependent anion channel was applied to a dry hydroxyapatite/celite (2:1, w/w) column (0.08 g/mg of protein) and eluted with buffer containing 10 mM Tris, pH 7.4, 50 mM NaCl, 20 mM sodium phosphate and 2% LDAO. The voltage-dependent anion channel-containing fractions (identified by Coomassie Blue staining) were collected, diluted 5-fold with 10 mM Tris, pH 7.4, and loaded onto a CM-cellulose column pre-equilibrated with 10 mM Tris, pH 7.4, and 0.5% n-octyl β-D-glucopyranoside (Bachem AG). The loaded column was then washed with the same equilibration buffer, and voltage-dependent anion channel was eluted with the same buffer containing 0.4 M NaCl.

Voltage-Dependent Anion Channel Recording and Analysis

Voltage-dependent anion channel was reconstituted into a planar lipid bilayer (PLB), recorded and analysed as described in Azoulay-Zohar (2004). Briefly, a PLB was prepared from soybean asolectin dissolved in n-decane (50 mg/ml). Purified voltage-dependent anion channel (approximately 1 ng) was added to the chamber defined as cis side. After one or few channels were inserted into the PLB, excess protein was removed by washing the cis chamber with 20 volumes of solution to prevent further incorporation. Currents were recorded under a voltage clump using a Bilayer Clamp BC-525B amplifier (Warner Instruments, Hamden, Conn., USA). Currents were measured with respect to the trans side of the membrane (ground). The currents were low-pass-filtered at 1 kHz using a Bessel filter (Frequency Devices, Haverhill, Mass., USA), and digitized on-line using a Digidata 1200-interface board and PCLAMP 6 software (Axon Instruments Inc., Union City, Calif., USA).

Transfection Experiments

CT26 cells were transfected with pcDNA3-HKII or pcDNA3, using FuGene HD transfection reagent (Roche, Basel, Switzerland), according to the manufacturer's instruction followed by selection using G418.

Statistical Analysis

Results are presented as mean±standard error of at least 3 independent experiments. Statistical significance was assessed using ANOVA test. $P<0.05$ was considered statistically significant and marked by asterix in the respective graphs.

Hexokinase-Mitochondria Association is a Molecular Target of Methyl Jasmonate

Example 1

Figure 1B:
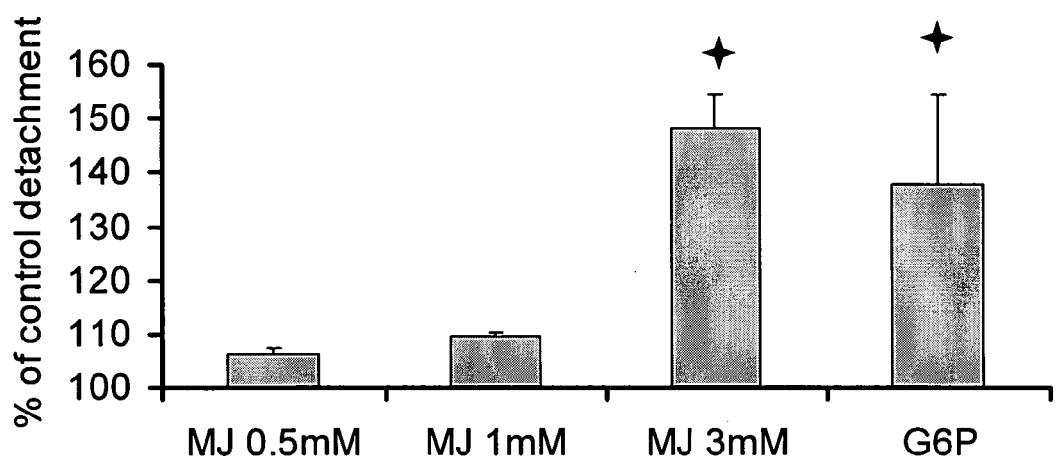
FIG. 1B. Methyl jasmonate (MJ) detaches hexokinase in a dose-dependent manner during 30 minutes of incubation; G6P at 0.5 mM served as a positive control.

Methyl Jasmonate Detaches Hexokinase from the Mitochondrial Fraction of Cancer Cells Methyl jasmonate perturbs mitochondria directly in a PTPC-dependent manner (Rotem, 2005). In order to determine whether methyl jasmonate is able to detach hexokinase from mitochondrial fraction isolated from CT-26 tumors, the activity of hexokinase in the supernatant of mitochondrial fraction treated for different time periods was measured. Mitochondrial fraction from a CT-26 tumor were incubated for either 10, 30 or 60 minutes with the various reagents at 37° C. The activity of unbound hexokinase was measured and compared to the activity of spontaneously detached hexokinase (control). Methyl jasmonate detached hexokinase in a time-dependent manner (FIG. 1A). Furthermore, analyses that were performed during 30 minutes of incubation showed that the detachment of hexokinase by methyl jasmonate was dose-dependent (FIG. 1B). On the contrary, the less cytotoxic derivative of methyl jasmonate, jasmonic acid (Fingrut, 2002), did not show considerable detachment of hexokinase from mitochondrial fraction.

Figure 1C:
FIG. 1C. Mitochondrial fraction supernatants from similar experiments were collected, separated on SDS-PAGE and probed with anti-HKI and anti-HKII antibodies.
Figure 1C:

In order to verify physical detachment of mitochondrial hexokinase, similar preparations were separated on SDS-PAGE, electroblotted to nitrocellulose membrane and probed with anti-HKI and anti-HKII antibodies. The release of both HKI and HKII were demonstrated (FIG. 1C).

Figure 2A:
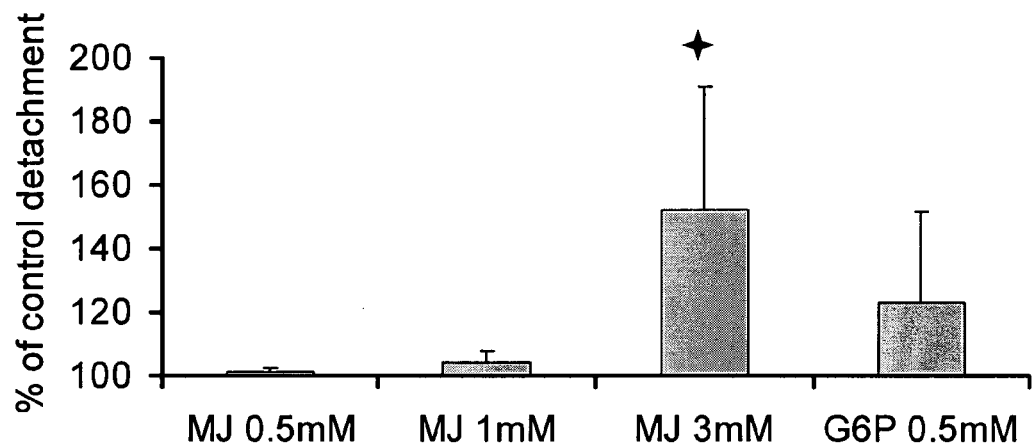
FIG. 2A. The mitochondrial fraction of Molt-4 cells.
Figure 2B:
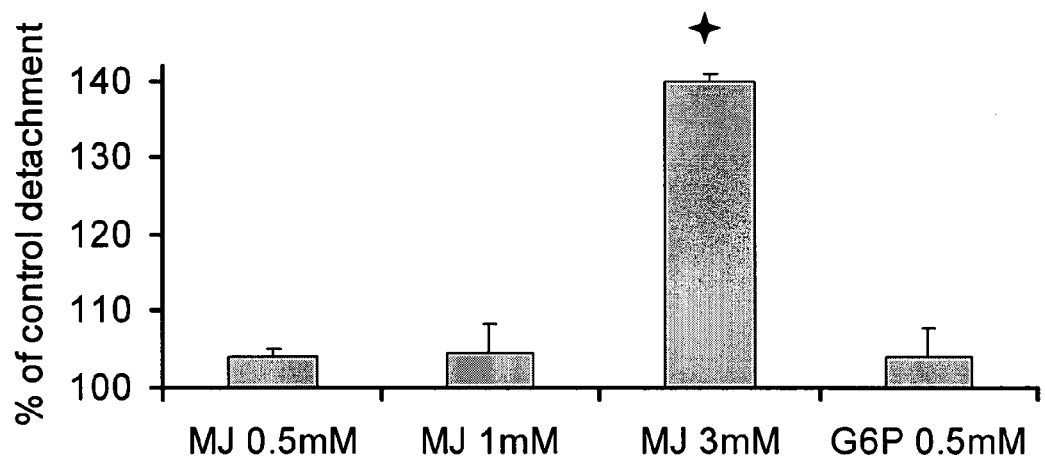
FIG. 2B. The mitochondrial fraction of BCL-1.
Figure 2C:
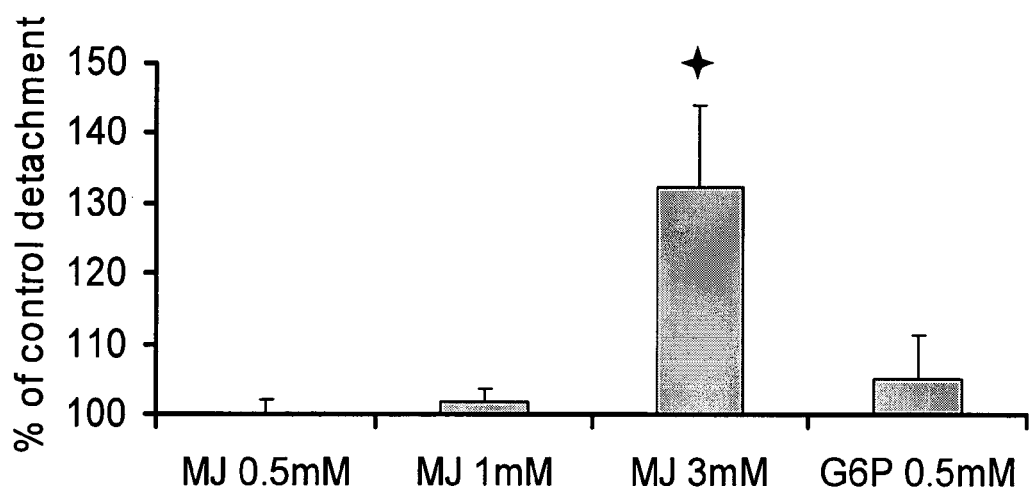
FIG. 2C. The mitochondrial fraction of B16 tumors. The supernatant of the experiments FIG. 2D, FIG. 2E, and FIG. 2F, respectively were separated on SDS-PAGE and probed with anti-HKI and anti-HKII antibodies.

Hexokinase detachment from mitochondrial fraction is not limited to CT-26 colon carcinoma. Mitochondrial fractions isolated from different cancer cells, namely Molt-4 cells, BCL-1 leukemic cells and B16 melanoma tumors were incubated for 30 minutes at 37° C., and the activity of unbound hexokinase was measured and compared to the activity of spontaneously (control) detached hexokinase. Methyl jasmonate detached hexokinase from mitochondrial fraction isolated from the three different cancer cells (FIGS. 2A-2C). The supernatant of the experiments were separated on SDS-PAGE and probed with anti-HKI and anti-HKII antibodies.

Figure 2D:
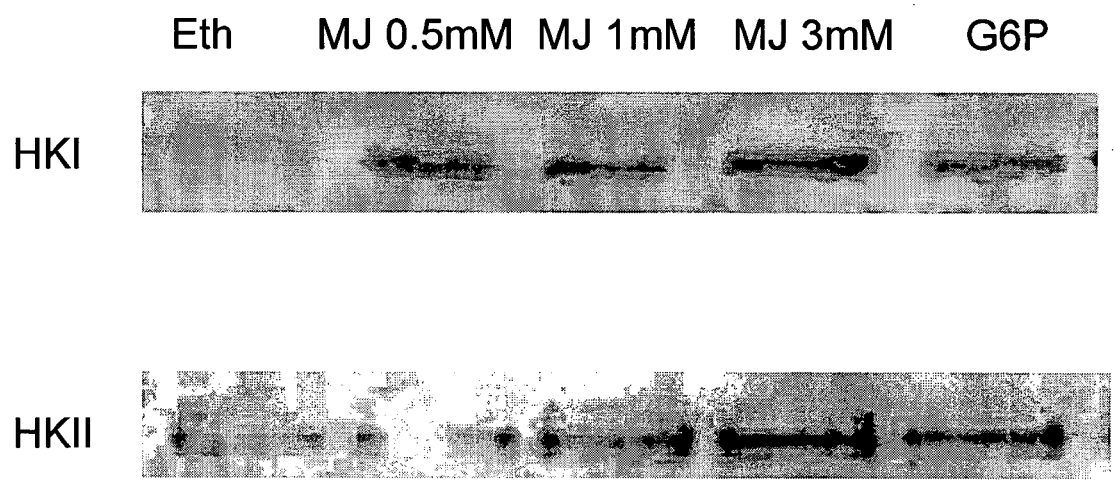
FIG. 2. Methyl jasmonate (MJ) detaches hexokinase (HK) from mitochondrial fraction isolated from various cancer cells.
Figure 2E:
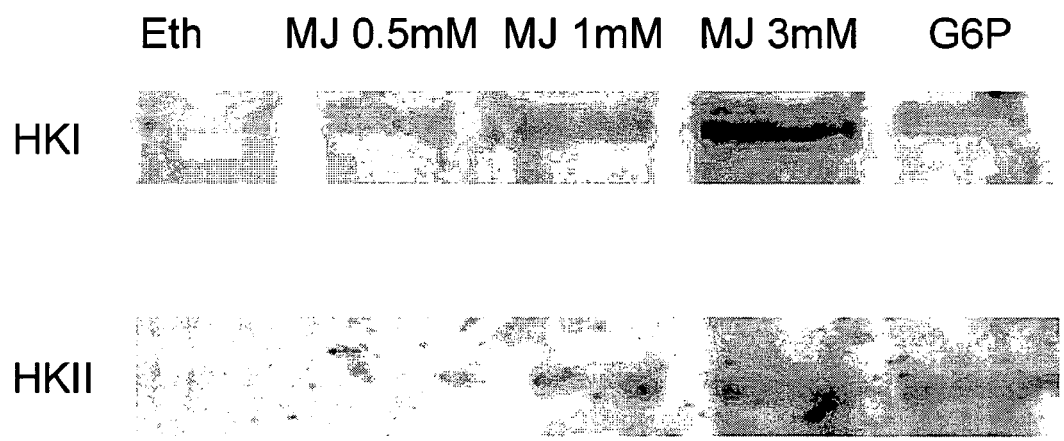
Figure 2F:
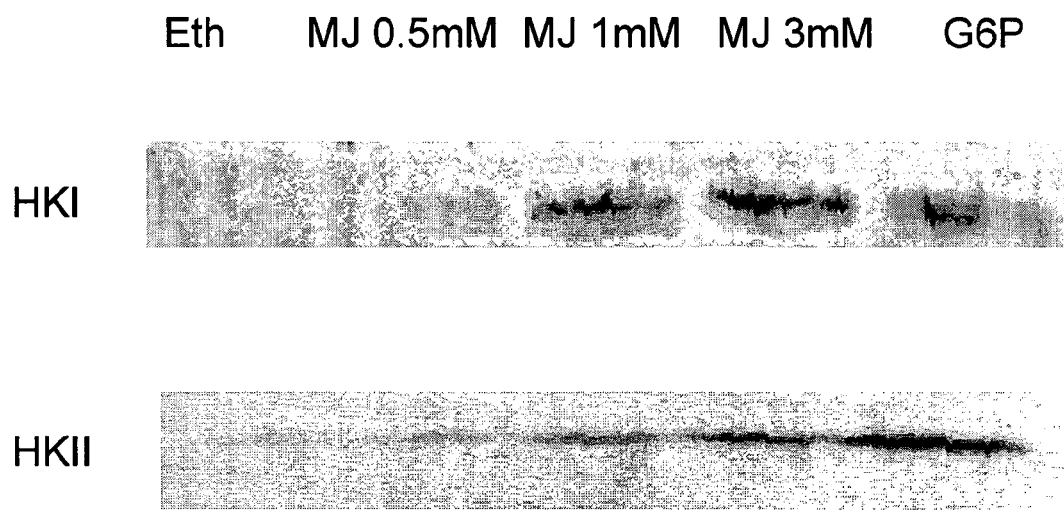

The detachment of hexokinase from mitochondrial fraction of the various cancer cells was further confirmed (FIGS. 2D-2F).

Example 2

Figure 3:
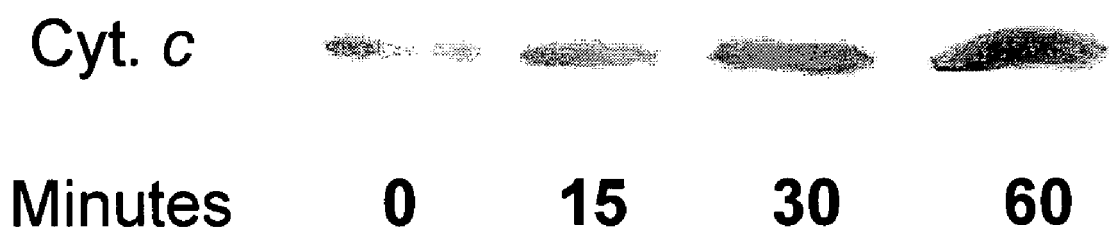
FIG. 3. Methyl jasmonate (MJ) causes time-dependent release of cytochrome c from the isolated mitochondrial fraction of CT-26 tumor. Mitochondrial fraction were treated with 3 mM methyl jasmonate (MJ) for the indicated periods of time and pelleted. The released cytochrome c was probed with specific antibodies.

Mitochondrial Damage and ATP Depletion Occur Simultaneously with Hexokinase Release from Mitochondrial Fraction Cytochrome c release from mitochondrial fraction isolated from CT-26 tumors occurred within the same time frame (15-60 minutes) required to detach hexokinase from mitochondria (FIG. 3). Methyl jasmonate caused time-dependent release of cytochrome c from the isolated mitochondrial fraction of CT-26 tumor. The release was probed using specific antibodies.

Figure 4A:
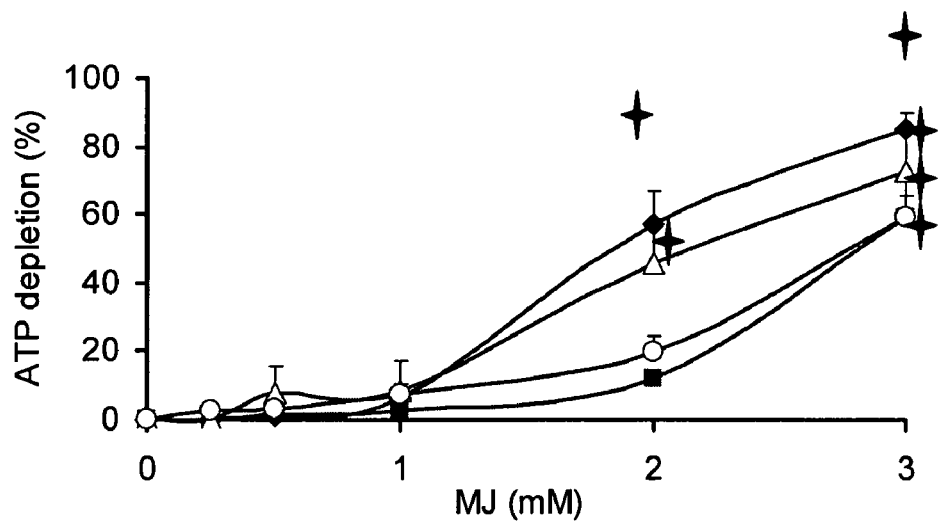
FIG. 4A. CT26 (full squares), Molt-4 (full rhombs), B16 (empty triangles) and BCL1 (empty circles) cells were exposed to the indicated methyl jasmonate (MJ) concentrations, and cellular ATP levels were determined.
Figure 4B:
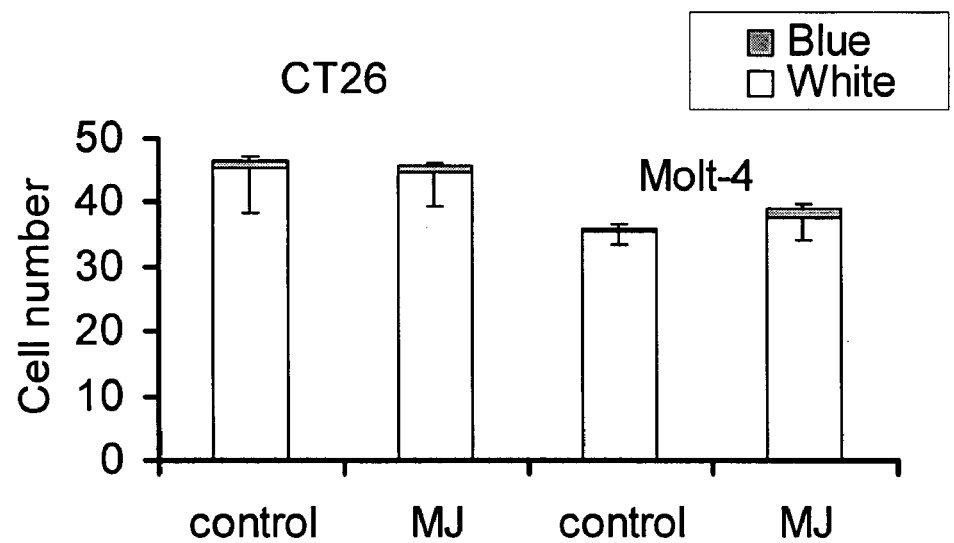
FIG. 4B. CT26 (left) and Molt-4 (right) cells were exposed to methyl jasmonate (MJ; 3 mM). Cells were counted following Trypan blue exclusion test. White and blue represent live and dead cells respectively.

In order to test the correlation between cellular ATP levels and the release of hexokinase from mitochondrial fraction different cancer cells, namely Molt-4 cells, BCL-1 leukemic cells and B16 melanoma tumors were exposed to various methyl jasmonate concentrations. FIG. 4A demonstrates that all three different cancer cell lines exhibited a significant and dose-dependent decrease of cellular ATP during 60 minutes of exposure to methyl jasmonate. CT26 and Molt-4 cells were then seeded in 24 well plates. CT26 cells were allowed to adhere over night. Cells were exposed to methyl jasmonate (MJ; 3 mM) for 1 hour. Trypan blue exclusion test was performed and cells were counted. Despite of the massive ATP depletion, cells exposed to 3 mM methyl jasmonate were still alive after 60 minutes (FIG. 4B). Although Molt-4 cells showed increased sensitivity with respect to CT26 tumor cells, in both cell lines ATP depletion preceded appearance of dead cells.

Example 3

Figure 5:
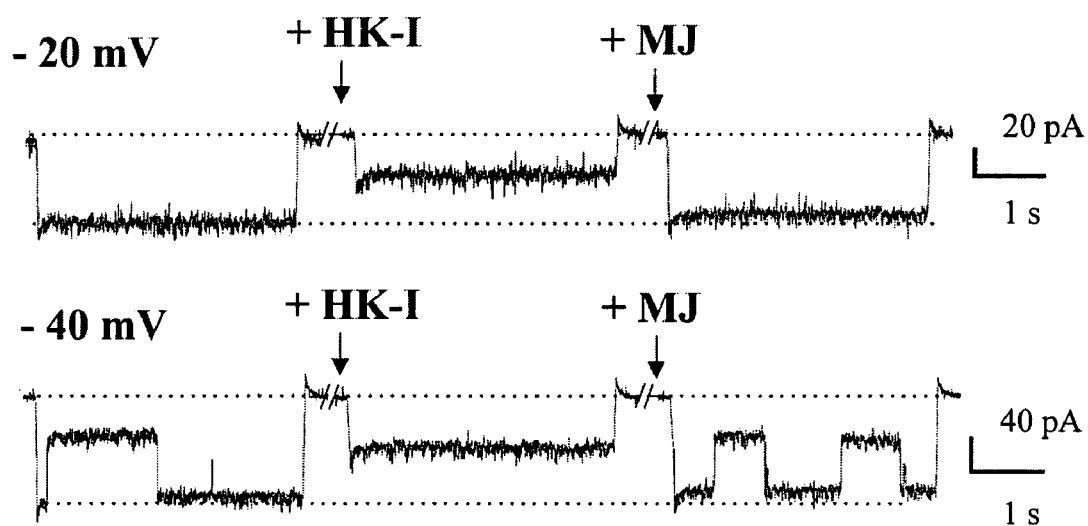
FIG. 5. Methyl jasmonate (MJ) disrupts hexokinase-I-Voltage dependent anion channel interactions. Voltage-dependent anion channel was reconstituted into a planar lipid bilayer. Currents, in response to a voltage step from 0 to −20 mV or −40 mV were recorded before and 10 minutes after the addition of hexokinase-I (HK-I; 20 mU/ml). Where indicated, methyl jasmonate (MJ; 3 mM) was added, and currents were recorded after 10 minutes.

Methyl Jasmonate Re-Opens Hexokinase-I-Closed Lipid Bilayer-Reconstituted Voltage-Dependent Anion Channels Mammalian HKI and HKII bind mitochondrial outer membrane via voltage-dependent anion channel (Azoulay-Zohar, 2004; Robey, 2006). The effect of methyl jasmonate on channel activity of purified mitochondrial voltage-dependent anion channel reconstituted into a planar lipid bilayer was studied under voltage clamp conditions (Azoulay-Zohar, 2004). The monitoring of voltage-dependent anion channel activity is a conventional method for examining voltage-dependent anion channel interactions with hexokinase and other agents (Shoshan-Barmats, 2005). Voltage-dependent anion channel was reconstituted into a planar lipid bilayer. Currents, in response to a voltage step from 0 to −20 mV or −40 mV were recorded in symmetrical solutions of 0.5 M NaCl before and 10 minutes after the addition of hexokinase-I (HK-I; 20 mU/ml). Where indicated, methyl jasmonate (MJ) at 3 mM was added, and currents were recorded after 10 minutes. The dashed lines indicate zero-current and maximal current levels (FIG. 5). The data are representative of 3 replicates. Methyl jasmonate at 3 mM concentration showed no effect on the current passing through voltage-dependent anion channel in response to voltages stepped from a holding potential of 0 mV to −40 mV. At relatively small membrane potentials (−20 mV), the conductance remained constant for up to 120 minutes of recording (FIG. 5). However, upon addition of purified HK-I, the open channel was stabilized in its low-conducting state. This effect of HK-I on voltage-dependent anion channel was reversed by the addition of methyl jasmonate, exhibiting the ability of methyl jasmonate to disrupt the interaction between hexokinase and voltage-dependent anion channel. Similar results were obtained when reconstituted voltage-dependent anion channel was exposed to −40 mV. HK-I promoted voltage-dependent anion channel closure and stabilized it at the sub-conductance state. Similarly, addition of methyl jasmonate led to re-opening of HK-I-closed channels (FIG. 5).

Example 4

Figure 6A:
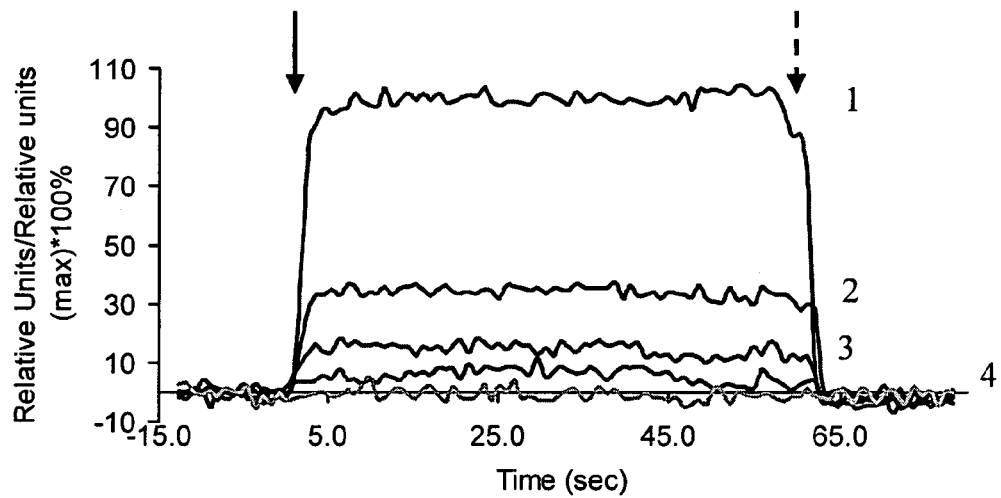
FIG. 6A. Methyl jasmonate binds to hexokinase in a dose-dependent manner: #1 represents 6 mM MJ; #2 represents 3 mM MJ; #3 represents 1.5 mM MJ; #4 represents 0.75 mM MJ; gray line represents 0.375 mM MJ.
Figure 6B:
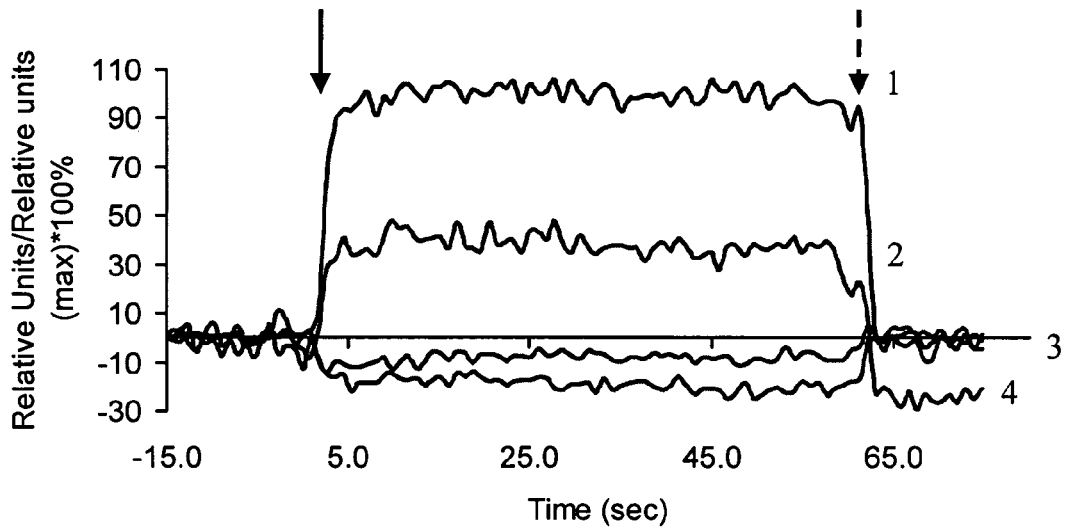
FIG. 6B. Methyl jasmonate binds to hexokinase but not to Rb IgG: #1 represents MJ at 6 mM; #2 represents MJ at 3 mM; #3 and #4 represent Rb IgG.

Methyl Jasmonate Interacts with Hexokinase in a Specific and Dose-Dependent Manner In order to probe a possible direct interaction of methyl jasmonate with hexokinase, a real time surface plasmon resonance analysis was performed. Methyl jasmonate was found to bind to purified rat brain HKI in a dose-dependent manner (FIG. 6A). However, the determination of the constant of dissociation was not possible because of the limited solubility of methyl jasmonate in the running buffer. FIG. 6B shows the verification of the specificity of binding through the use of an irrelevant protein—Rb IgG—(#3 and #4) instead of hexokinase (#1 and #2).

Figure 6C:
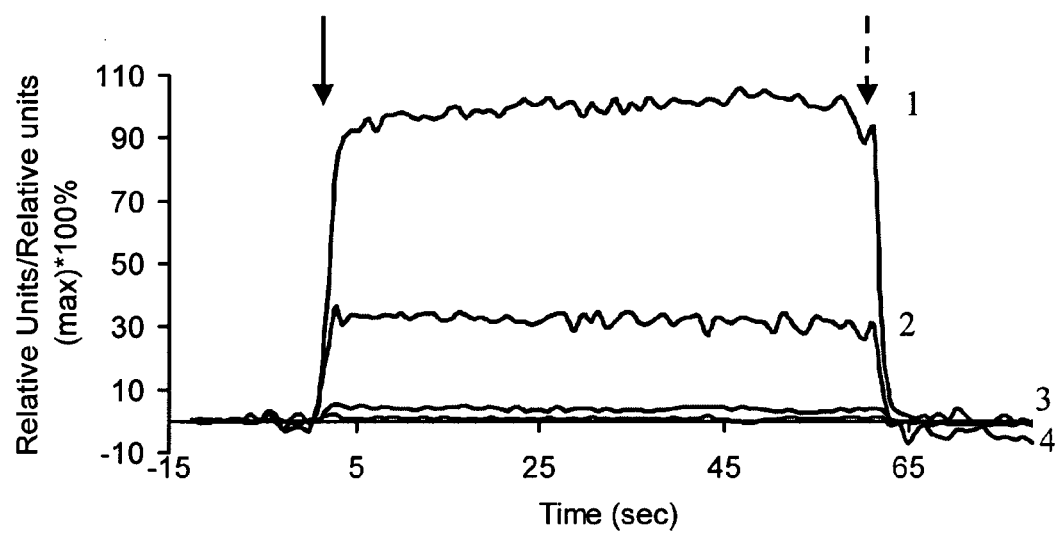
FIG. 6C. Jasmonic acid (JA) does not bind to hexokinase: #3 represents 6 nM JA; #4 represents 3 mM JA; MJ 6 mM (#1) and 3 mM (#2) served as positive controls. Solid and dotted arrows represent the start and the end points of the injection of analytes, respectively.

In order to further demonstrate the specificity of methyl jasmonate, jasmonic acid which has lower cytotoxicity than methyl jasmonate (Fingrut, 2002; Fingrut, 2005; Rotem, 2005) perturbed mitochondria to a lesser extent, and was shown to be less effective than methyl jasmonate at detaching hexokinase from mitochondrial fraction (FIG. 1C) was tested under similar conditions. FIG. 6C demonstrates that jasmonic acid did not bind hexokinase at all under these conditions (#3 and #4 vs. #1 and #2 of methyl jasmonate). Thus, methyl jasmonate interacts with hexokinase in a specific manner.

Dissociation of the Hexokinase-Mitochondria Interaction Mediates Methyl Jasmonate-Induced Mitochondriotoxicity and Cytotoxicity Example 5

Methyl Jasmonate Induces Swelling Selectively in Hexokinase-Rich Mitochondria

Figure 7A:
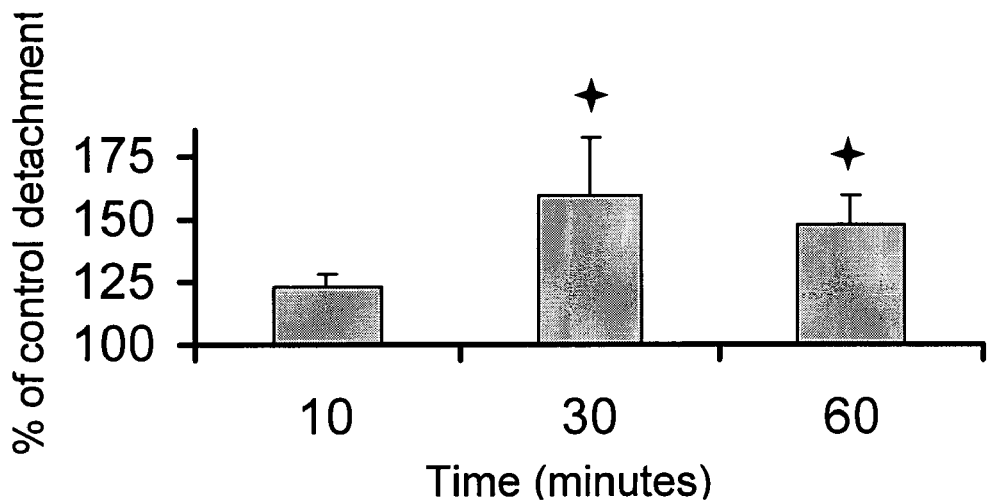
FIG. 7A. MJ (3 mM) detaches hexokinase in a time-dependent manner.
Figure 7B:
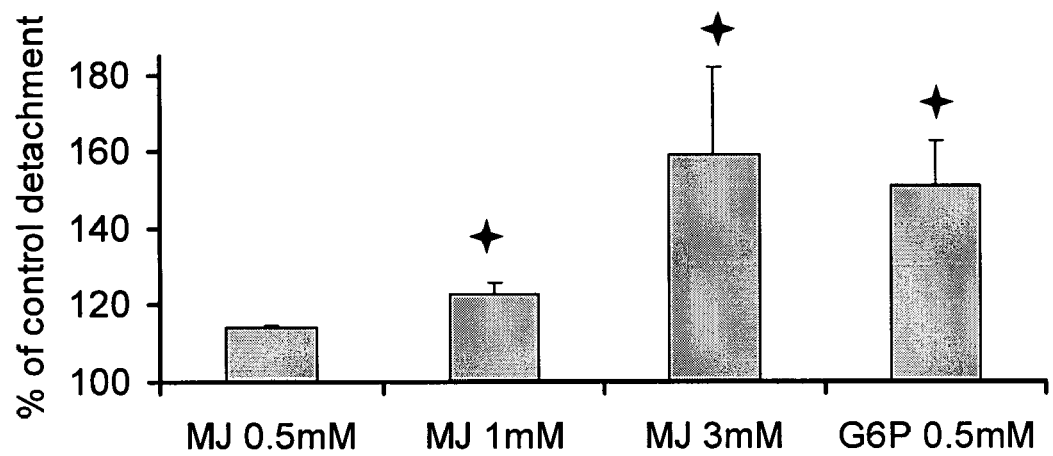
FIG. 7B. MJ detaches hexokinase in a dose-dependent manner during 30 minutes of incubation. G6P served as a positive control.
Figure 8A:
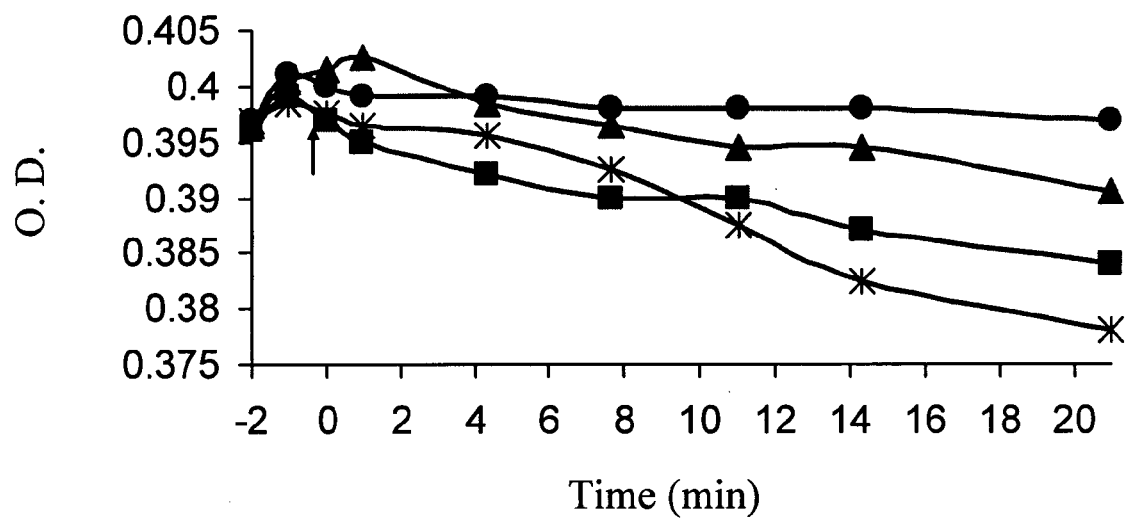
FIG. 8A. Mitochondrial fraction of mouse brain.
Figure 8B:
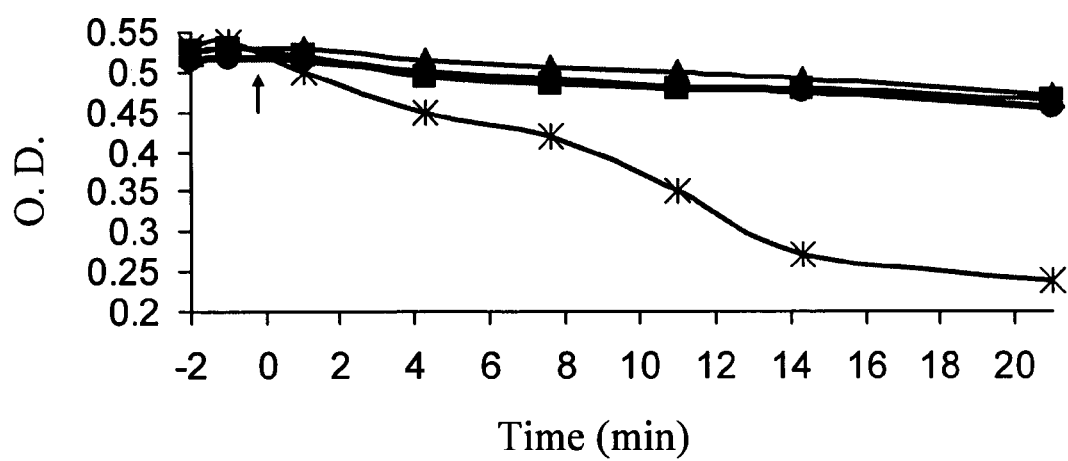
FIG. 8B. Mitochondrial fraction of mouse liver. Methyl jasmonate (MJ; 1 mM, squares), Jasmonic acid (JA; 1 mM, triangles), or buffer (circles) were applied on mitochondria, and optical density was monitored. Taxol (70 µM, stars) served as a positive control (Varbiro, 2001).

In order to examine the consistency of the relationship between the ability of methyl jasmonate to detach bound hexokinase and mitochondrial damage, methyl jasmonate was tested in mouse brain in comparison to mouse liver. The comparison was performed due to known differences of mitochondrial hexokinase content between mouse brain vs. its liver. It is well established in the art that brain mitochondrial fraction is rich in bound hexokinase, while liver mitochondrial fraction is essentially devoid of it (Wilson, 1995). First, the ability of methyl jasmonate to detach hexokinase from mitochondrial fraction isolated from mouse brain was demonstrated to be both time-dependent as well as dose dependent (FIG. 7A and FIG. 7B respectively). Mitochondrial fractions were incubated for either 10, 30 or 60 minutes at 37° C. The activity of unbound hexokinase was measured and compared to the activity of spontaneously (control) detached hexokinase. Consequently, the ability of methyl jasmonate to induce swelling in mitochondrial fraction isolated from mouse brain and liver was tested. As predicted by the above-mentioned relationship, methyl jasmonate and, to a marginal extent, jasmonic acid led to swelling in brain (FIG. 8A) but not in liver (FIG. 8B) mitochondrial fraction.

Example 6

Figure 9A:
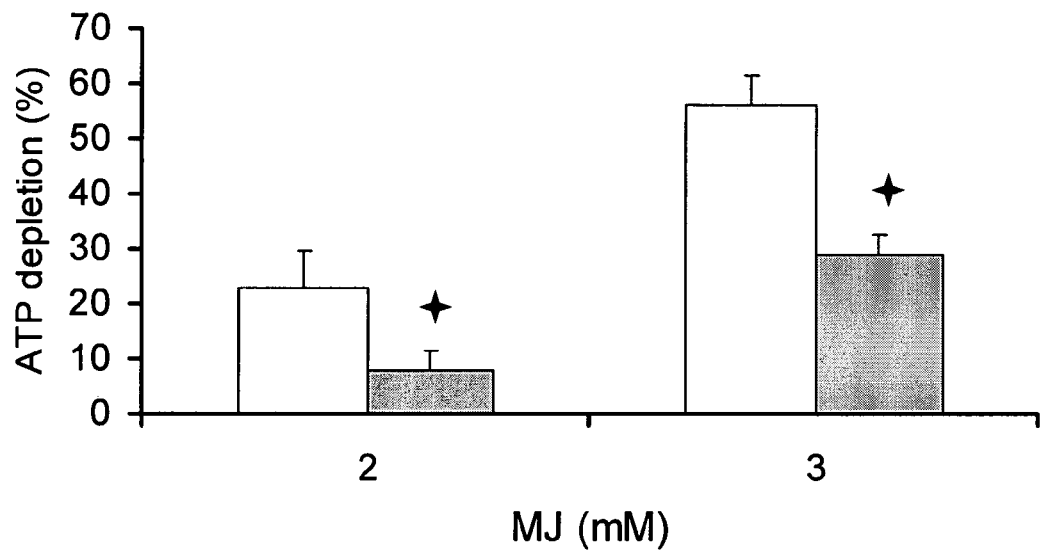
FIG. 9A. Methyl jasmonate (MJ) exposure prior to ATP determination.
Figure 9B:
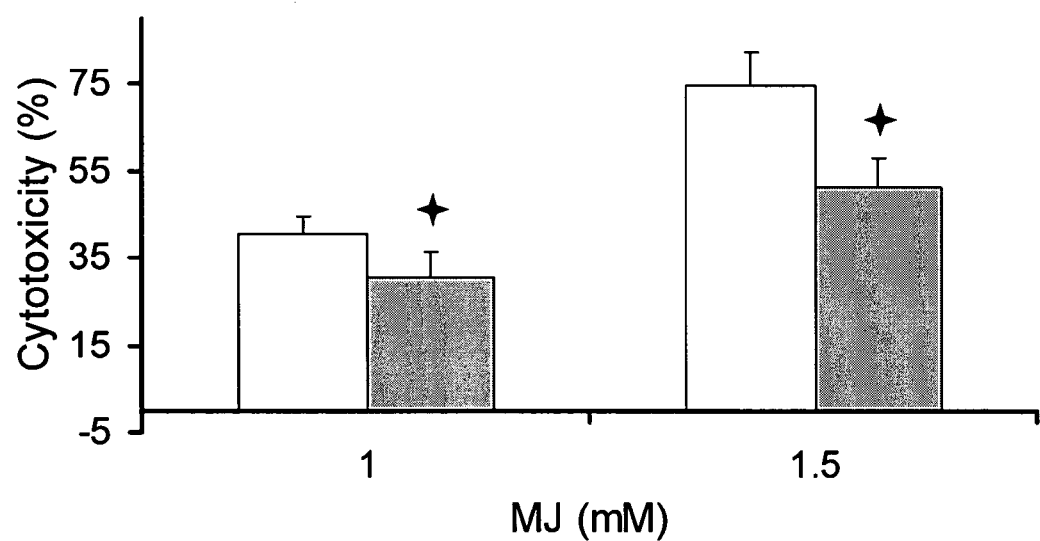
FIG. 9B. Methyl jasmonate (MJ) exposure prior to cytotoxicity determination.
Figure 9C:
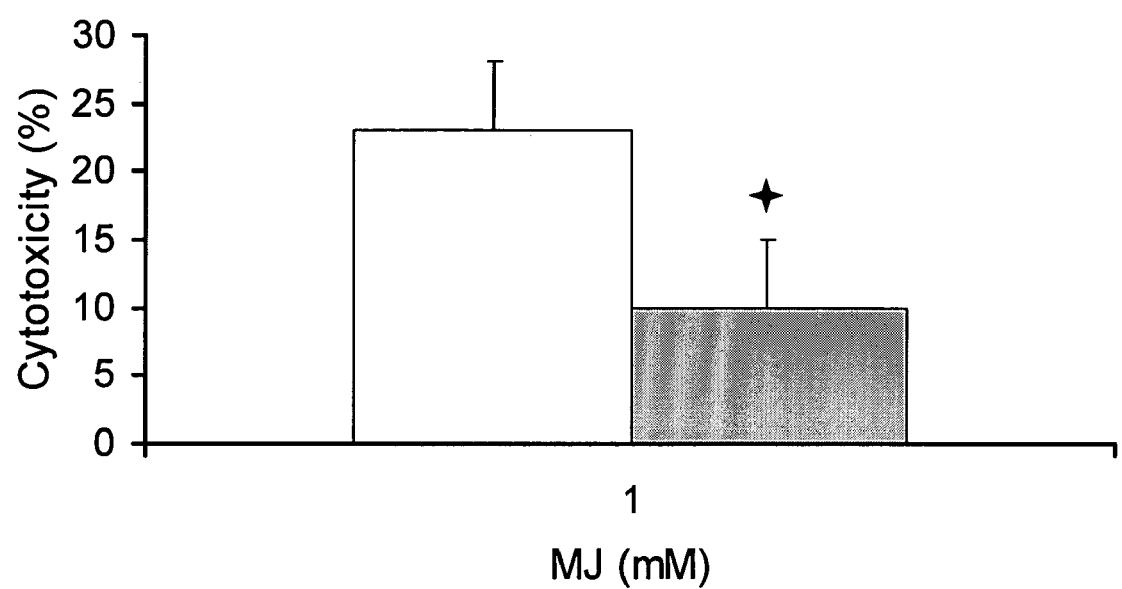
FIG. 9C. Staurosporine exposure prior to cytotoxicity determination. The data are representative of 3 replicates.

Over Expression of Hexokinase Protects from Methyl Jasmonate-Induced Cytotoxicity To examine the effect of hexokinase over-expression on methyl jasmonate action, CT26 cells were transfected with plasmids, pcDNA3-HKII or pcDNA3, encoding for hexokinase II over-expression and a control plasmid, respectively (Zaid, 2005). Cells were seeded in 96-well plates and allowed to adhere. Cells were exposed to methyl jasmonate for 60 minutes prior to ATP determination (FIG. 9A) and for 24 hours prior to cytotoxicity determination by the hemacolor method (FIG. 9B). As shown in FIG. 9A and in FIG. 9B, both the 60-minute depletion of cellular ATP levels and overnight cytotoxicity induced by methyl jasmonate were decreased in cells with higher expression of hexokinase II (grey) compared to control (white). Moreover, the cytotoxicity induced by exposure to 3.75 µM staurosporine (a positive control; Azoulay-Zohar, 2004) for 3 hours prior to cytotoxicity determination by the hemacolor method was similarly decreased by hexokinase II over-expression (FIG. 9C).

Example 7

Hexokinase Detachment by Novel Compounds as Compared to Methyl Jasmonate Correlates with their Ability to Cause Tumor Cell Death The correlation between the ability of novel compounds to cause hexokinase detachment from mitochondria as compared to methyl jasmonate and their ability to cause tumor cell death as compared to methyl jasmonate was examined. A series of six organically synthesized compounds (jasmonate derivatives) having molecular weights below 2000 Dalton (compounds A, B, C, D, E, F) were analyzed for their ability to cause hexokinase detachment from tumor cell mitochondria as described above. The compounds were then ranked together with methyl jasmonate (MJ) for their ability to cause hexokinase detachment.

Figure 10:
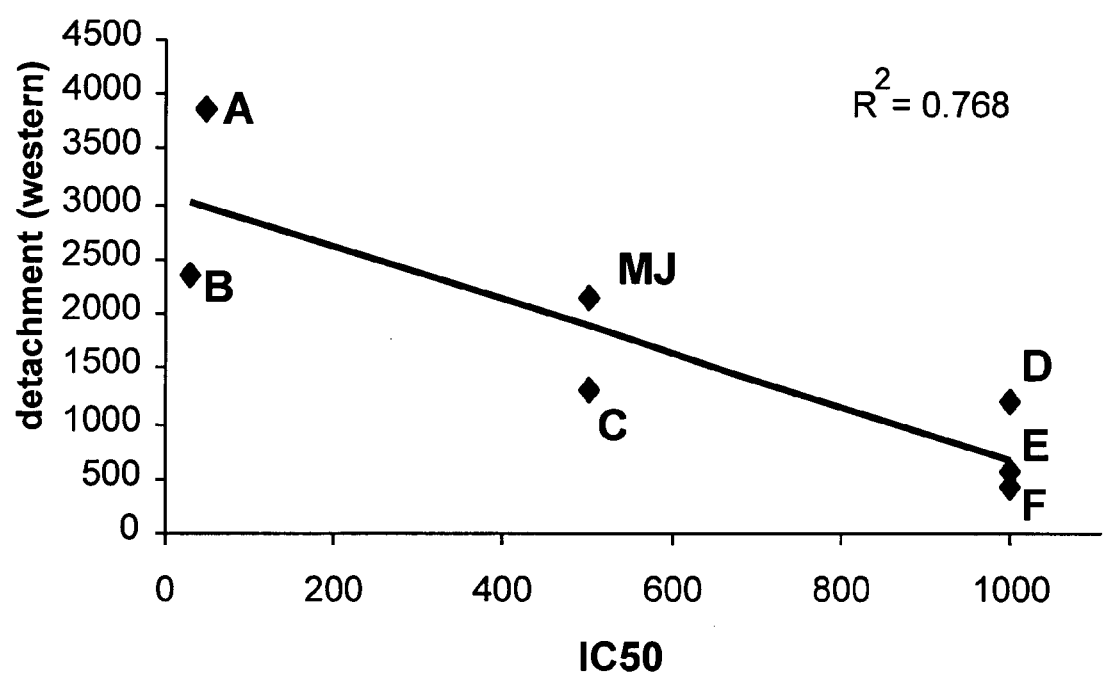
FIG. 10. Comparison of hexokinase detachment ability by novel compounds as compared to methyl jasmonate is indicative of their ability to cause tumor cell death. Correlation between hexokinase detachment activity for each compound (vertical axis) vs. its IC50 for cytotoxicity on Molt-4 cells (horizontal axis). A-F represent six different jasmonate derivatives; MJ=methyl jasmonate. Linear correlation was analyzed and assessed using the $R^2$ factor.

The anti-tumor activity of these compounds was further assessed by analyzing their cytotoxic activity on Molt-4 cells. The correlation between hexokinase detachment and induced tumor cell death of the ranked compounds A to F and methyl jasmonate was assessed by plotting the hexokinase detachment activity as a function of cytotoxicity on Molt-4 cells. FIG. 10 shows a strong correlation between hexokinase detachment ability of the compounds as compared to methyl jasmonate and their ability to cause tumor cell death.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Azoulay-Zohar H., Israelson A., Abu-Hamad S., and Shoshan-Barmatz V. (2004). In self-defense: hexokinase promotes voltage-dependent anion channel closure and prevents mitochondria-mediated apoptotic cell death. Biochem. J. 377, 347-355.

Fingrut O., and Flescher E. (2002). Plant stress hormones suppress the proliferation and induce apoptosis in human cancer cells. Leukemia 16, 608-616.

Fingrut O., Reischer D., Rotem R., Goldin N., Altboum I., Zan-Bar I., and Flescher E. (2005). Jasmonates induce nonapoptotic death in high-resistance mutant p53-expressing B-lymphoma cells. Br. J. Pharmacol. 146, 800-808.

Flescher E. (2005). Jasmonates—a new family of anti-cancer agents. Anticancer Drugs 16, 911-916.

Galuzzi L., Larochette N., Zamzami N., and Kroemer G. (2006). Mitochondria as therapeutic targets for cancer chemotherapy. Oncogene 25, 4812-4830.

Goldin N., Heyfets A., Reischer D., and Flescher E. (2007). Mitochondria-mediated ATP depletion by anti-cancer agents of the jasmonate family. J. Bioenerg. Biomemb. 39, 51-57.

Heyfets A., and Flescher E. (2007). Cooperative cytotoxicity of methyl jasmonate with anti-cancer drugs and 2-deoxy-d-glucose. Cancer Lett. 50, 300-310.

Ishii Y., Kiyota H., Sakai S., and Honma Y. (2004). Induction of differentiation of human myeloid leukemia cells by jasmonates, plant hormones. Leukemia 18, 1413-1419.

Kim J. H., Lee S. Y., Oh S. Y., Han S. I., Park H. G., Yoo M. A., and Kang H. S. (2004). Methyl jasmonate induces apoptosis through induction of Bax/Bcl-XS and activation of caspase-3 via ROS production in A549 cells. Oncol. Rep. 12, 1233-1238.

Mathupala S. P., Ko Y. H., and Pedersen P. L. (2006). Hexokinase II: Cancer's double-edged sword acting as both facilitator and gatekeeper of malignancy when bound to mitochondria. Oncogene 25: 4777-4786.

Pastorino J. G., Shulga N., and Hoek J. B. (2002). Mitochondrial binding of hexokinase II inhibits Bax-induced cytochrome c release and apoptosis. J. Biol. Chem. 277, 7610-7618.

Reischer D., Heyfets A., Shimony S., Nordenberg J., Kashman Y., and Flescher E., (2007). Effects of natural and novel synthetic jasmonates in experimental metastatic melanoma. Br. J. Pharmacol. 150, 738-749.

Robey R. B., and Hay N. (2006). Mitochondrial hexokinases, novel mediators of the antiapoptotic affects of growth factors and Akt. Oncogene 25, 4683-4696.

Rotem R., Heyfets A., Fingrut O., Blickstein D., Shaklai M., and Flescher E. (2005). Jasmonates: novel anticancer agents acting directly and selectively on human cancer cell mitochondria. Cancer Res. 65, 1984-1993.

Shoshan-Barmatz V., and Israelson A. (2005). The voltage-dependent anion channel in endoplasmic/sarcoplasmic reticulum: characterization, modulation and possible function. J Membr Biol. 204, 57-66.

Varbiro G., Veres B., Gallyas F., and Sumegi B. (2001). Direct effect of Taxol on free redical formation and mitochondrial permeability transition. Free Radic. Biol. Med. 31, 548-558.

Wilson J. E. (1995). Hexokinases. Rev. Physiol. Biochem. Pharmacol. 126, 65-198.

Zaid H., Abu-Hamad S., Israelson A., Nathan I., and Shoshan-Barmatz V. (2005). The voltage-dependent anion channel-1 modulates apoptotic cell death. Cell Death Differ. 12, 751-760.

The invention claimed is:

1. An assay for identifying a chemical compound having a potential anti-tumor effect comprising comparing the activities of the compound and a jasmonate derivative known to have anti-tumor activity in at least one of the following: dissociating hexokinase from mitochondria, interfering with hexokinase binding to a voltage dependent anion channel, and binding to hexokinase directly; and selecting a compound having an equal or greater anti-tumor activity as compared with at least one anti-tumor activity of said jasmonate derivative selected from the group consisting of: dissociating hexokinase from mitochondria, interfering with hexokinase binding to a voltage dependent anion channel, and binding to hexokinase directly, thereby identifying a chemical compound having a potential anti-tumor effect.

2. The assay according to claim 1, wherein the jasmonate derivative is methyl jasmonate.

3. The assay according to claim 1, wherein the chemical compound is a jasmonate derivative other than methyl jasmonate.

4. An assay for identifying a chemical compound having a potential anti-tumor effect comprising: introducing the compound into a cell free system comprising mitochondria; measuring the ability of said compound to induce dissociation of a hexokinase from the mitochondria; comparing the dissociation of hexokinase in the presence of said compound to the dissociation achieved by a jasmonate derivative known to have anti-tumor activity; and selecting a compound having an equal or greater dissociation as compared with said jasmonate derivative, thereby identifying a chemical compound having a potential anti-tumor effect.

5. The assay according to claim 4, wherein the compound selectively induces tumor cell death.

6. The assay according to claim 4, wherein the jasmonate derivative is methyl jasmonate.

7. The assay according to claim 4, wherein the chemical compound is a jasmonate derivative other than methyl jasmonate.

8. An assay for identifying a chemical compound having a potential anti-tumor effect comprising: measuring the direct binding of the compound to at least one hexokinase subtype; comparing this binding to the binding achieved by a jasmonate derivative known to have anti-tumor activity, and selecting a chemical compound having an equal or greater binding as compared with said jasmonate derivative, thereby identifying a chemical compound having a potential anti-tumor effect.

9. The assay according to claim 8, wherein the compound selectively induces tumor cell death.

10. The assay according to claim 8, wherein the jasmonate derivative is methyl jasmonate.

11. The assay according to claim 8, wherein the chemical compound is a jasmonate derivative other than methyl jasmonate.

* * * * *